US008029493B2

(12) United States Patent
Asfora

(10) Patent No.: US 8,029,493 B2
(45) Date of Patent: Oct. 4, 2011

(54) METHOD FOR ASPIRATING A SPACE WITHIN A BODY

(75) Inventor: Wilson T. Asfora, Sioux Falls, SD (US)

(73) Assignee: Medtronic PS Medical, Inc., Goleta, CA (US)

( * ) Notice: Subject to any disclaimer, the term of this patent is extended or adjusted under 35 U.S.C. 154(b) by 0 days.

(21) Appl. No.: 12/495,357

(22) Filed: Jun. 30, 2009

(65) Prior Publication Data

US 2009/0264811 A1    Oct. 22, 2009

Related U.S. Application Data

(60) Division of application No. 11/546,656, filed on Oct. 12, 2006, now Pat. No. 7,553,290, which is a continuation-in-part of application No. 09/633,573, filed on Aug. 4, 2000, now abandoned, which is a continuation-in-part of application No. 29/105,951, filed on Jun. 4, 1999, now Pat. No. Des. 435,291.

(51) Int. Cl.
*A61M 31/00* (2006.01)

(52) U.S. Cl. ...................................................... 604/506
(58) Field of Classification Search .............. 604/27–28, 604/35, 167.01–167.02, 500, 506
See application file for complete search history.

(56) References Cited

U.S. PATENT DOCUMENTS

| 4,014,333 | A | * | 3/1977 | McIntyre | 604/43 |
| 4,646,752 | A | * | 3/1987 | Swann et al. | 600/561 |
| 5,954,687 | A | * | 9/1999 | Baudino | 604/48 |
| 6,228,088 | B1 | * | 5/2001 | Miller et al. | 606/80 |

* cited by examiner

*Primary Examiner* — Theodore Stigell

(57) ABSTRACT

Methods for aspirating a space within the body of a patient, such as the subdural space, including providing an evacuating port device having an evacuating lumen in fluid communication with the space in the body. A port aspiration device is mounted on the evacuating port device, creating fluid communication between an aspiration channel of the port aspiration device and the evacuating lumen. An instrument is positioned in the aspiration channel so that the instrument is capable of entering the evacuating lumen of the evacuating port device. The instrument can dispense medication and/or remove materials from the lumen or the space in the body. The evacuating port device can be mounted to a patient's skull.

13 Claims, 15 Drawing Sheets

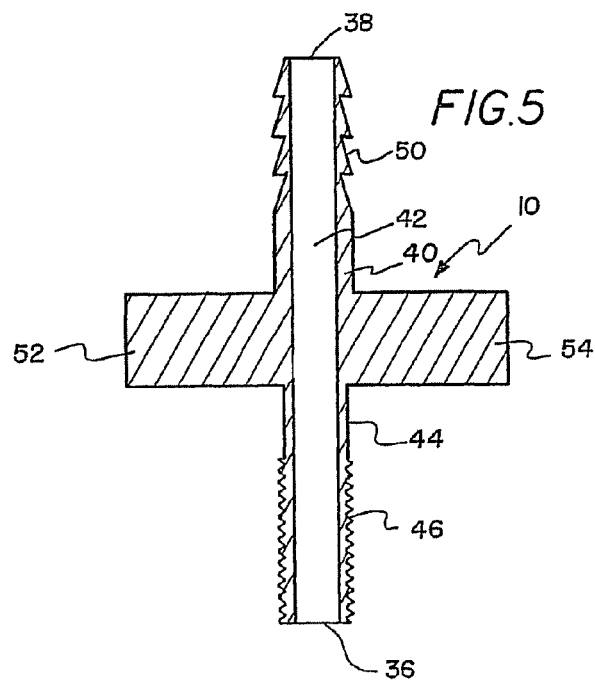
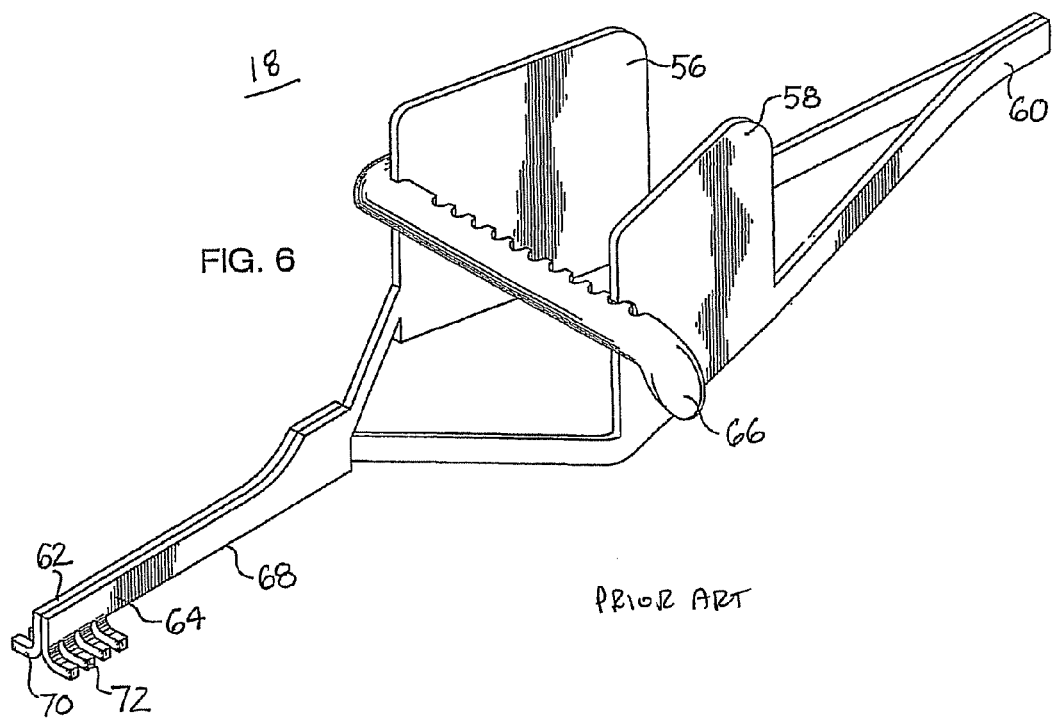
PRIOR ART

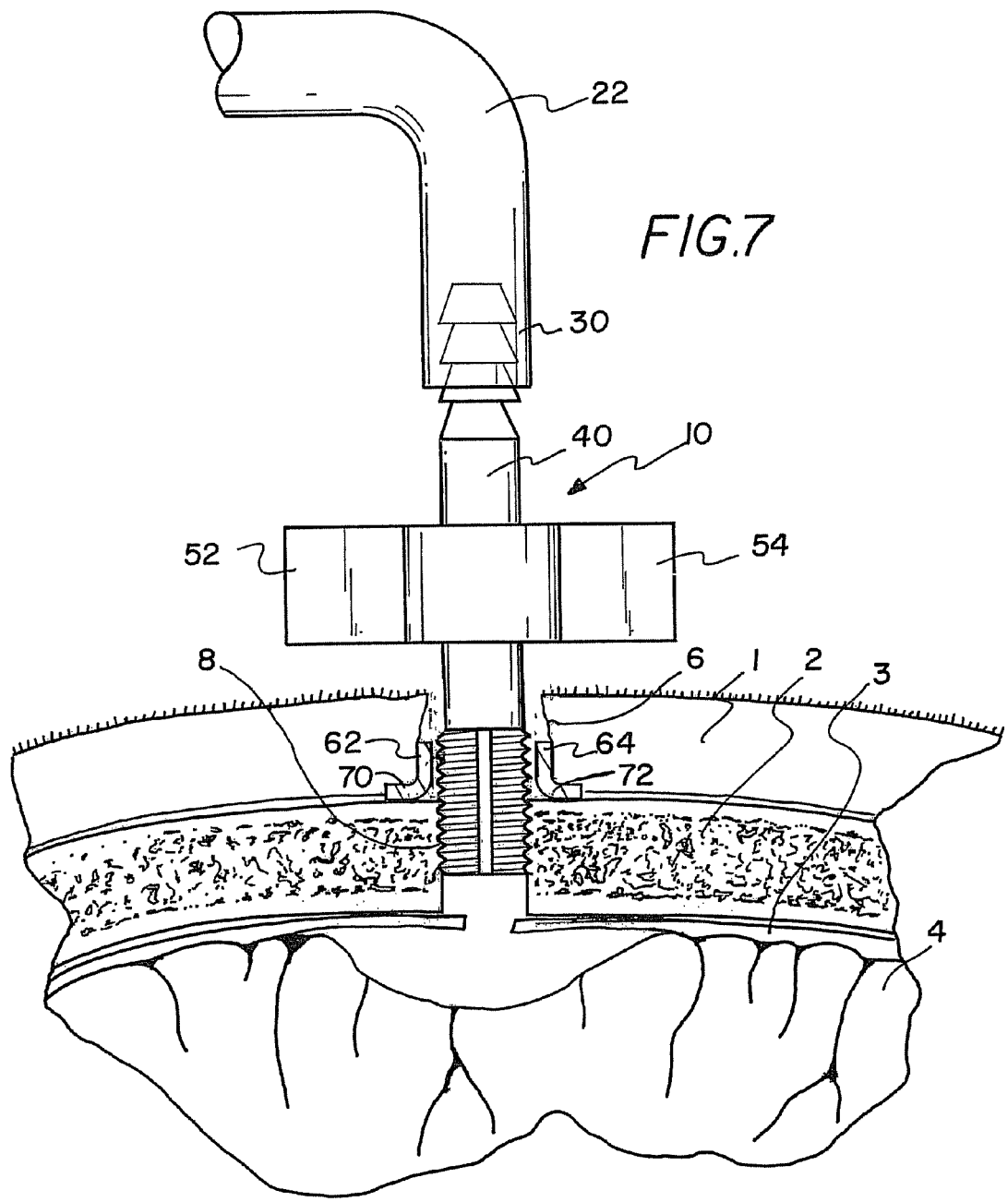

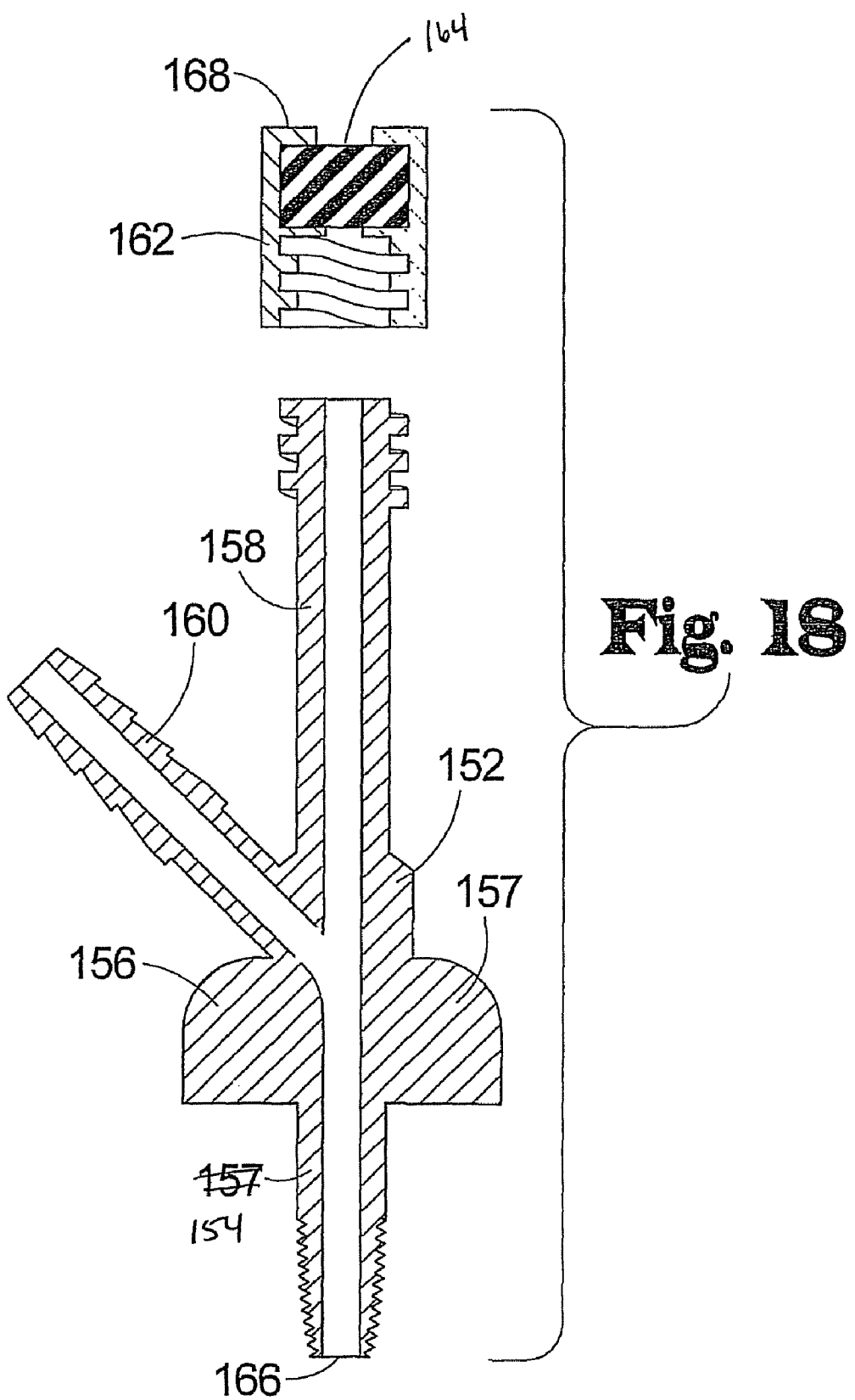

METHOD FOR ASPIRATING A SPACE WITHIN A BODY

CROSS-REFERENCE TO RELATED APPLICATIONS

This application is a divisional of U.S. application Ser. No. 11/546,656 and now U.S. Pat. No. 7,553,290, filed Oct. 12, 2006, which is a continuation-in-part of U.S. application Ser. No. 09/633,573, filed Aug. 4, 2000, which is a continuation-in-part of U.S. application Ser. No. 29/105,951, filed Jun. 4, 1999 and now U.S. Pat. No. D435,291; the disclosures of these patent applications are incorporated by reference herein in their entireties.

BACKGROUND

The present disclosure relates to systems for removing fluids from the subdural region of a patient and more particularly pertains to a new subdural evacuating port aspiration system for aspirating an evacuating port device useful for removing subdural fluid accumulations in a manner that is minimally invasive and promotes decompression, expansion, and recovery of the brain.

The subdural space of the human head is the space located between the brain and the lining of the brain, which is referred to as the dura mater (hereinafter referred to as the "dura"). Hemorrhages on the surface of the brain, for example, may cause a condition known as a subdural hematoma. The subdural hemorrhages may have a number of causes. For example, elderly persons may be more susceptible to subdural hemorrhages because as the brain ages it tends to become atrophic and the subdural space between the brain and the dura gradually enlarges. Bridging veins between brain and dura frequently stretch and rupture as a consequence of relatively minor head injuries, thus giving rise to a collection of blood in the subdural space. Further, severe linear deceleration of the brain can result in the brain moving excessively with respect to the dura, often causing rupture of the bridging veins or the blood vessels on the surface of the brain, which can in turn cause subdural hemorrhages in the "normal", young, and otherwise healthy brain.

These subdural blood collections can be classified as acute subdural hematomas, subacute subdural hematomas, and chronic subdural hematomas. Acute subdural hematomas, which are associated with major cerebral trauma, generally consist primarily of fresh blood. Subacute subdural hematomas are generally associated with less severe injuries than those underlying the acute subdural hematomas. Chronic subdural hematomas are generally associated with even less severe, or relatively minor, injuries. The chronic subdural hematomas tend to be less dense liquid consisting of very diluted blood.

Another condition involving a subdural collection of fluid is a hygroma, which is a collection of cerebrospinal fluid (sometimes mixed with blood) beneath the dura, usually in an encapsulation or cyst.

One form of treatment for acute subdural hematomas is the performance of a craniotomy operation. This operation entails the removal (with eventual replacement) of a large portion of the skull, opening of the dura, and evacuation of the collection of blood. The craniotomy frequently necessitates the placement of a subdural drain, which comprises a tube extending through the hole created by the craniotomy and into the subdural space for removing any additional accumulation of blood or fluid. The craniotomy is a highly invasive procedure that generally involves significant risk to the patient and an extended recovery period.

Since the subacute and chronic types of subdural hematomas primarily comprise collections of liquid, the treatment may range from the performance of a craniotomy to the use of a burr hole. The burr hole operation generally comprises boring in the skull a hole that is smaller than the portion of skull removed in a craniotomy. The burr hole generally has a diameter of about 14 to 18 mm. Through the burr hole, extensive washing of the subdural space may be carried out. Frequently, a drain needs to be left in place through the burr hole, with the end of the drain being in communication with the surface of the brain in order to allow for postoperative drainage of any further accumulations of fluid. Again, the patient is exposed to a fairly invasive procedure and a relatively long recovery period.

The aforementioned drains are typically used in combination with the application of negative pressure through the tube of the drain. The typical level of the negative pressure applied by the drains frequently causes further hemorrhage of the brain, especially if the end of the tube should come in contact with the surface of the brain. Further, recurrence of subdural hematomas and hygromas is quite common in chronic cases as the brain generally fails to expand to fill the enlarged subdural space created by the collection of fluid. If the subdural space remains enlarged after removal of the fluid, additional fluid tends to collect in the enlarged subdural space. The aforementioned treatment techniques do not actively contribute to re-expansion of the brain within the dura, and therefore do little to prevent the re-accumulation of fluid in the enlarged subdural space.

Furthermore, blood clots or other obstructions occasionally block the passages of devices (such as drains) that are used to remove fluids from the skull. The known devices typically do not address the need to clear these blockages from the passages or the affected inside the skull, or even periodically administer substances to the affected area inside the skull, without having to remove the devices from the skull.

The subdural evacuating port system according to the present disclosure substantially departs from the conventional concepts and designs and methods of the prior art, and in so doing provides an apparatus and method primarily developed for the purpose of removing subdural fluid accumulations in a manner that is minimally invasive and promotes decompression, expansion, and recovery of the brain.

SUMMARY

In view of the foregoing disadvantages inherent in the known techniques and systems for removing fluids from the subdural region of a patient now present in the prior art, the present disclosure provides a new subdural evacuating port system with a device and method of use wherein the same can be utilized for removing subdural fluid accumulations in a manner that is minimally invasive and promotes the decompression, expansion, and recovery of the brain.

The disclosure includes a procedure for treating substantially liquid subdural fluid collections in a manner that is minimally invasive and does not involve touching the brain. Significantly, the procedures of the disclosure promote brain expansion within the dura by creating a homogeneous, negative pressure throughout the subdural space from which the fluid collection has been removed.

The disclosure is especially effective when used on patients having a subdural space filled with fluid that is substantially liquid without significant coagulation of the fluid, including acute patients that are taking anticoagulants to enhance the fluidity of the matter that has accumulated in the subdural space.

The disclosure contemplates a kit for evacuating a collection of fluid from a subdural space of a patient having a scalp. The kit may include a subdural evacuating port device having a proximal end and a distal end. The subdural evacuating port device has a tubular portion with a lumen extending between the proximal and distal ends. An exterior surface of the proximal end of the tubular portion has self-tapping threads formed thereon for cutting threads into a skull. Retaining means on the exterior surface of the tubular portion adjacent to the distal end are provided for engaging an interior surface of a conduit with a flexible wall to releasably retain the conduit on the distal end of the tubular portion. A pair of wings extend outwardly from the tubular portion in substantially opposite directions. The kit also includes means for performing placement of the subdural evacuating port device in the patient. The means for performing placement of the subdural evacuating port device may include means for preparing an operative site on the scalp of the patient. The means for performing placement of the subdural evacuating port device may include means for opening an operative site on the patient. The means for performing placement of the subdural evacuating port device may include means for establishing an operative area on the patient. The kit may also include packaging for removably securing other elements of the kit. The means for performing placement of the subdural evacuating port device may include means for maintaining an operative area on the patient.

In another aspect of the disclosure, a subdural evacuation port aspiration system is disclosed for permitting aspiration of a subdural evacuation port device that defines an evacuation lumen. The evacuation port aspiration system may comprise an evacuation port aspiration device for facilitating aspiration of the evacuation port device when the port aspiration device is mounted on the evacuation port device. The port aspiration device defines an aspiration channel, and further comprises a mounting portion that is configured to mount on the evacuation port device. The mounting portion defines a first portion of the aspiration channel. The port aspiration device further comprises an aspiration portion for receiving an aspiration device, and that defines a second portion of the aspiration channel. The port aspiration device still further comprises a negative pressure connection portion for connecting to a negative pressure source, and defines a third portion of the aspiration channel.

In still another aspect of the disclosure, a method of aspirating a space within the body of a patient is disclosed, and may include providing a subdural evacuating port device having an evacuating lumen in fluid communication with the space in the body, and mounting a port aspiration device on the evacuating port device. Mounting of the port aspiration device may include creating fluid communication between an aspiration channel of the port aspiration device and the evacuating lumen of the evacuating port device. The method may further include positioning an instrument in the aspiration channel of the port aspiration device so that the instrument is capable of entering the evacuating lumen of the evacuating port device.

There has thus been outlined, rather broadly, features of the disclosure in order that the detailed description thereof that follows may be better understood, and in order that the present contribution to the art may be better appreciated. There are additional features of the disclosure that will be described hereinafter and which will form the subject matter of the claims appended hereto.

In this respect, before explaining at least one embodiment of the disclosure in detail, it is to be understood that the disclosure is not limited in its application to the details of construction and to the arrangements of the components set forth in the following description or illustrated in the drawings. The disclosure is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present disclosure. It is important, therefore, that the claims be regarded as including such equivalent constructions insofar as they do not depart from the spirit and scope of the present disclosure.

For a better understanding of the disclosure, its operating advantages and the specific objects attained by its uses, reference should be made to the accompanying drawings and descriptive matter in which there are illustrated preferred embodiments of the disclosure.

BRIEF DESCRIPTION OF THE DRAWINGS

The disclosure may be better understood and objects other than those set forth above will become apparent when consideration is given to the following detailed description thereof. Such description makes reference to the annexed drawings wherein:

FIG. 5 is a schematic sectional view of the subdural evacuating port device of FIG. 1.

FIG. 6 is a schematic perspective view of a retractor useful in the techniques of the present disclosure.

FIG. 7 is a schematic sectional view of a portion of a patient's skull and brain area with the subdural evacuating port device of FIG. 1 mounted on the skull.

FIG. 18 is a schematic sectional view of the system of FIG. 17 with a removable, adjustable cap.

DETAILED DESCRIPTION

Figure 1:
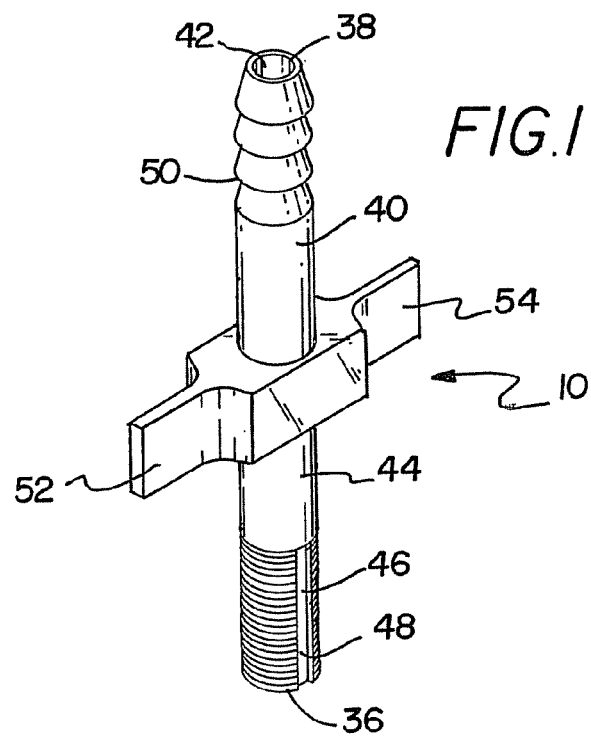
FIG. 1 is a schematic perspective view of a subdural evacuating port device in accordance with principles of the present disclosure.
Figure 2:
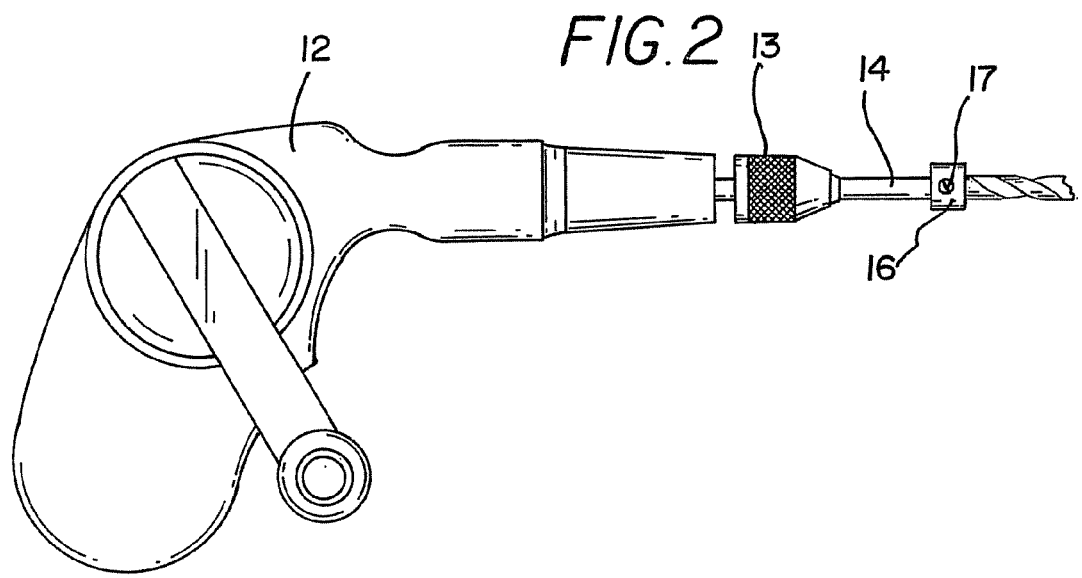
FIG. 2 is a schematic side view of a drill bit useful in the techniques of the present disclosure.

With reference now to the drawings, and in particular to FIGS. 1 through 18 thereof, a new subdural evacuating port system and subdural evacuating port aspiration system embodying the principles and concepts of the present disclosure will be described.

As best illustrated in FIGS. 1 through 7, one system in accordance with aspects of the present disclosure generally includes a subdural evacuating port device 10, and contemplates a kit for evacuating a collection of fluid from a subdural space of a patient that incorporates the subdural evacuating port device. The system also contemplates a method for utilizing the subdural evacuating port device and elements of the kit for removing fluid from the subdural space while facilitating the recovery of the patient's brain.

Elements useful in practicing the disclosure include the subdural evacuating port device 10, a drill device 12, a drill bit 14 for mounting on the drill device, a stop collar 16 for mounting on the drill bit, a retractor device 18, a negative pressure source 20, and a conduit 22.

The drill device 12 is provided for rotating the drill bit 14. The drill bit 14 is mountable on the drill device 12 in a suitable manner, such as by an adjustable chuck assembly 13. The chuck assembly 13 of the drill device 12 is most preferably rotated by manual means (e.g., turned by the surgeon's hand), but optionally the chuck assembly 13 may be driven by motorized means.

The drill bit 14 is adapted for removably mounting on the drill device 12, and the drill bit 14 can be sized for creating an opening of a suitable size in the skull of the patient, as will be discussed in greater detail below. Illustratively, the drill bit 14 is formed of a stainless steel material. The stop collar 16 can be provided for selectively limiting the maximum penetration of the tip of the drill bit 14 into the skull of the patient. The stop collar 16 can be selectively lockable in a variety of longitudinal positions along the length of the drill bit 14 depending upon the depth of penetration needed to produce an opening through the skull without injuring the brain.

The stop collar 16 is provided with a channel for receiving a portion of the drill bit 14, and the stop collar 16 has a set screw 17 for extending into the channel and abutting against the drill bit 14 for locking the stop collar 16 in a selected longitudinal position. Illustratively, one suitable material for the stop collar 16 is a nylon, such as DELRIN.

The retractor device 18 is provided for holding back the edges of an incision made through the scalp of the patient. The retractor device 18 is useful for reducing the possibility of contact between the drill bit 14 and the scalp when the drill bit 14 is inserted through the incision for boring into the skull, and thus reduces any damage resulting from such contact. In some embodiments, the retraction device is of the type known as a "Holzheimer" retractor (see FIG. 6). The "Holzheimer" retractor generally has two arms 56, 58 that are joined together at proximal ends of the arms to form an apex 60. The arms 56, 58 extend away from the apex 60 and terminate at free ends 62, 64 of the arms 56, 58. Preferably, the free ends 62, 64 of the arms 56, 58 are spaced such that the arms 56, 58 form a substantially V-shaped structure. A locking member 66 may be included on the retractor for selectively locking the arms at a desired spacing. The "Holzheimer" retractor 18 has a lower edge 68 for inserting into the incision. A tab 70, 72 may be provided on each of the arms 56, 58 adjacent to the lower edge 68 at a location separated from the apex 60 of the clip. The tabs 70, 72 preferably lodge themselves below the outer surface of the scalp to help hold the clip in place with respect to the incision during the period when the incision needs to be held open. Optionally, but less preferably, retraction of the scalp may be performed by other known types of surgical retractors, such as, for example, a "Mastoid" retractor, a "Gelpi" retractor, or a "Heiss" retractor.

The negative pressure device 20 is provided for creating a uniform negative pressure condition in the subdural space of the patient. The negative pressure device exerts a suction for imparting a uniform partial vacuum in the subdural space. The magnitude of the negative pressure condition created is relatively low for exerting a gentle suction in the subdural space. The substantial uniformity of the negative pressure is considered important for promoting the gradual re-expansion of the brain in the subdural space. The magnitude of the negative pressure exerted by a suitable negative pressure source is approximately 0.8 inch to 1 inch of mercury (Hg) with respect to atmospheric pressure. It may be appreciated that a lower level (e.g., less than 0.8 inches of mercury) of negative pressure may be used, although the effectiveness of the fluid removal may be reduced. While relatively higher levels of negative pressure may be used (such as up to approximately 1.2 inches of mercury), significantly higher levels of negative pressure can hamper the recovery of the brain and the associated tissues, by, for example, not allowing the brain to fully re-expand to its condition prior to the fluid accumulating in the subdural space. The relatively low level of negative pressure permits the negative pressure condition to be maintained in the subdural space for a relatively extended period of time for removing any further collection of fluid, as well as promoting a gradual expansion of the brain in the subdural space during the healing process.

Figure 3:
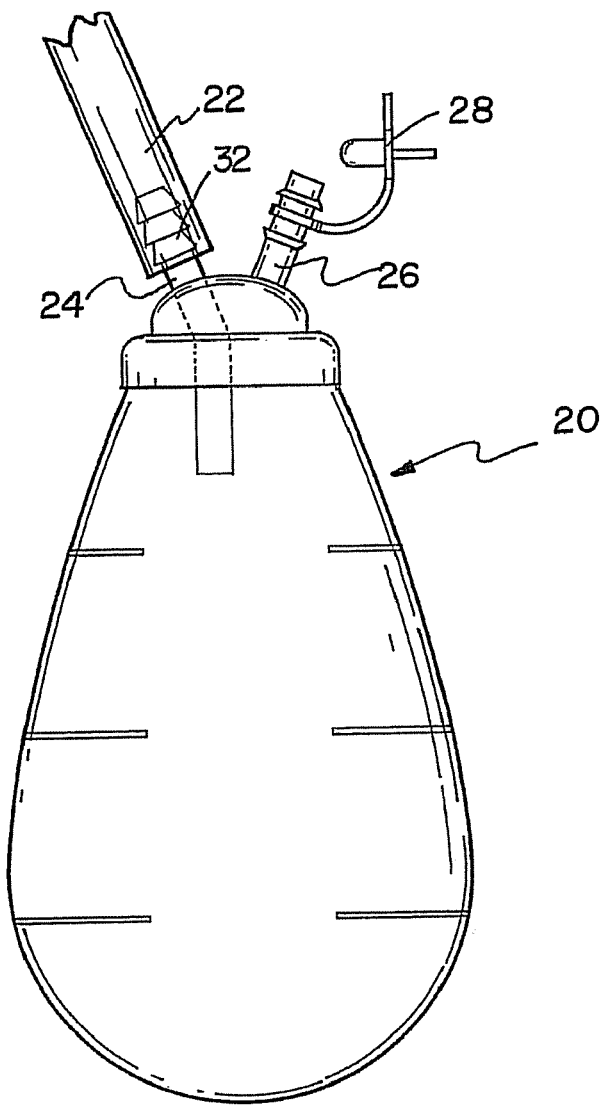
FIG. 3 is a schematic side view of a bulb useful in the techniques of the present disclosure.
Figure 4:
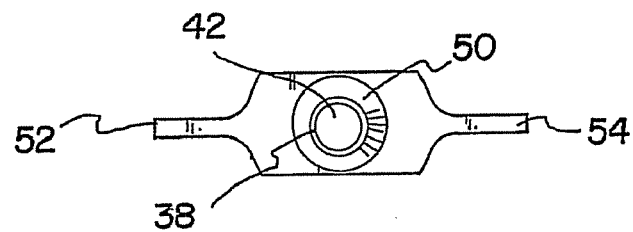
FIG. 4 is a schematic end view of the subdural evacuating port device of FIG. 1.

A useful negative pressure source is a device commonly referred to as a Jackson-Pratt bulb (see FIG. 3). The Jackson-Pratt bulb 20 has an interior and a pair of openings 24, 26. More particularly, the bulb 20 has a primary opening 24 and a secondary opening 26, and each opening 24, 26 extends between the interior and an exterior of the bulb. A check valve (not shown) is provided on the bulb 20 in communication with the primary opening 24 for resisting exit of fluid (e.g., gas or liquid) from the interior to the exterior of the bulb through the primary opening while permitting fluid flow into the interior through the primary opening. A cap 28 may be provided for selectively closing the secondary opening 26 of the bulb 20 thus requiring any fluid entering the interior to enter through the primary opening 24.

The conduit 22 may be provided for fluidly connecting the subdural evacuating port device 10 with the negative pressure source 20. Preferably, the conduit 22 connects the primary opening 24 of the Jackson-Pratt bulb 20 with the subdural evacuating port device. The conduit 22 has first 30 and second 32 ends, and the first end 30 is removably connectable to the subdural evacuating port device 10 and the second end 32 is removably connectable to the primary opening 24 of the Jackson-Pratt bulb 20. The conduit 22 may comprise flexible tubing of the type commonly used for draining fluids from the body, such as, for example, tubing formed from a silicone material. Illustratively, a length of tubing between approximately 2.4 and 3 feet (approximately 75 cm and 90 cm) is suitable.

A feature of the disclosure is the subdural evacuating port device 10 for penetrating the skull of the patient. The port device 10 includes a substantially tubular portion 40 with a lumen 42 that extends between a proximal end 36 and a distal end 38 of the port device 10. An exterior surface 44 of the proximal end 36 of the tubular portion 40 is preferably provided with self-tapping threads 46 formed thereon for cutting threads into the skull of the patient as the proximal end 36 is inserted into an opening 8 in the patient's skull 2 and the port device 10 is rotated in the opening. Illustratively, a longitudinal groove 48 may extend through the self-tapping threads 46 to produce thread cutting surfaces on the exterior surface 44. An exterior surface 44 of the distal end 38 of the tubular portion 40 preferably has a plurality of annular barbs 50 formed thereon for retaining the conduit 22 on the distal end 38.

The subdural evacuating port device 10 includes a pair of wings 52, 54 extending outwardly from the tubular portion 40 which facilitate finger rotation of the tubular portion 40 in the opening 8 of the skull 2 during the threading of the opening by the self-tapping threads 46 of the port device 10. The wings 52, 54 extend in substantially opposite directions for enhancing finger grippability of the wings. The wings 52, 54 may be mounted on the tubular portion 40 at a location substantially medially between the proximal 36 and distal 38 ends of the tubular portion 40, between the self-tapping threads 46 and the annular barbs 50.

In one illustrative embodiment of the port device 10, the diameter of the exterior surface 44 of the tubular portion 40 measures approximately 6 mm. The lumen 42 has a diameter of approximately 3.8 mm. The length of the tubular portion 40 from the distal end 38 to the proximal end 36 is approximately 45 mm. The width between the tips of the wings 52, 54 is approximately 23 mm, and the width of the wings 52, 54 is approximately 5 mm in some constructions. The self-tapping threads 46 may extend approximately 10 mm from the proximal end 36, and the annular barbs 50 may extend approximately 15 mm from the distal end 38.

The method aspects of the disclosure permits evacuation of a collection of fluid from the subdural space within the skull 2 of a patient. One of the initial acts of the method includes determining the region of the scalp 1 of the patient that is adjacent to the location of the collection of fluid in the subdural space. Preferably, the region is located on the patient's scalp 1 where the collection of fluid has the greatest dimension or measurement in the subdural space of the skull 2. The location of the greatest dimension of the fluid collection may be determined by performing an imaging study of the head of the patient using, for example, computerized tomography or magnetic resonance imaging to determine the extent of the collection of fluid. Once the greatest dimension of the collection of fluid is determined, the location of the opening to be made through the skull 2 to the subdural cavity is selected on the scalp 1 at a substantially central location corresponding to the greatest dimension of the collection of fluid.

The scalp 1 of the patient may be infiltrated with an anesthetic such as by injecting the anesthetic into the scalp 1 in the region where the subdural collection of fluid has the greatest dimension. Illustratively, the anesthetic may be lidocaine or epinephrine, or other suitable anesthetic.

An incision 6 is created in the scalp 1 to expose the bone of the skull 2 of the patient. The incision 6 extends through the scalp 1, the subcutaneous tissue, the galea, and the periosteum. The retractor device 18 is introduced into the incision 6 for holding the scalp 1 adjacent to the incision away from the operating area. An opening 8 is created in the skull 2 of the patient using the drill bit 14 mounted in the drill device 12. The size of the opening 8 formed in the skull may be approximately 3 to 8 mm in diameter. The opening 8 in the skull can be approximately 5 to 7 mm in diameter. The appropriate size opening can be approximately 6 mm in diameter. The size of the drill bit 14 is such that it will create a suitable size opening in the skull.

The dura 3 may then be penetrated by incising the dura of the patient using, for example, a unipolar cautery device. The underlying membranes may be transected with the unipolar cautery device.

Fluid that has collected in the subdural space is removed from the space through the incision in the dura 3. This removal can be performed through the use of the subdural evacuating port device 10. The proximal end 36 of the subdural evacuating port device 10 is introduced into the opening 8 in the skull 2. The port device 10 is rotated in the opening 8 such that the self-tapping threads 46 engage the sides of the opening 8 and pull the proximal end 36 into the opening 8 and secure the port device 10 against unintentional withdrawal of the device 10 from the opening 8. The dura 3 may be penetrated by the proximal end 36 of the port device 10 for placing the lumen 42 in fluid communication with the subdural area, and any collection of fluid in a subdural space.

A substantially uniform negative pressure condition is created in the subdural space. This negative pressure condition can be created through the lumen 42 of the subdural evacuating port device 10 of the disclosure. The first end 30 of the conduit 22 is connected to the distal end 38 of the subdural evacuating port device, with the annular barbs 50 retaining the conduit 22 on the port device 10. The second end 32 of the conduit 22 is connected to the negative pressure source. The primary opening 24 of a Jackson-Pratt bulb 20 is connected to the second end 32 of the conduit 22. To produce the negative pressure condition in the conduit 22 and the lumen 42 of the port device 10, the Jackson-Pratt bulb 20 is compressed (such as by hand gripping of the bulb) with the cap 28 removed from the secondary opening 26 to expel as much air from the bulb as possible. The cap 28 is then placed over the secondary opening 26, and the expansion of the resilient bulb from the collapsed condition produces a negative pressure condition in the interior of the bulb as well as the conduit 22 and the lumen 42 of the port device 10.

The negative pressure condition created in the lumen 42 of the port device 10 tends to draw fluid collected in the subdural space through the lumen 42 and into the conduit 22 and into the interior of the bulb 20. The fluid collected in the interior of the bulb 20 may be periodically emptied from the bulb, and the negative pressure condition may be reapplied to the subdural space through the port device 10 using the bulb 20. The negative pressure condition may be removed when drainage from the subdural space is no longer observed, or the desired re-expansion of the brain in the subdural space has occurred, or as is determined to be medically advisable. To remove the subdural evacuating port device 10, the device 10 is rotated (e.g., using the wings 52, 54) such that the threads 46 move the port device 10 out of the opening 8.

In another aspect of the disclosure, a subdural evacuation port aspiration system 80 (shown in FIGS. 8 through 18) permits aspiration of the evacuation port device 10 as well as an internal body space that is in communication with the port device 10. As described above, the evacuation port device 10 defines the evacuating lumen 42 that is in fluid communication with the subdural space of the patient for the purposes of relieving pressure in the subdural space, as well as other purposes permitted by the port device 10. In some circumstances, it may be desirable to access the lumen 42 of the port device 10 while a conduit remains connected to the port device 10 and without significantly altering the negative pressure condition in the subdural space. The access may be for the purposes of, for example, clearing blood clots from the evacuating lumen 42 or the area just outside of the lumen 42, or for administering drugs or other medicaments to the subdural area via the port device 10.

Figure 8:
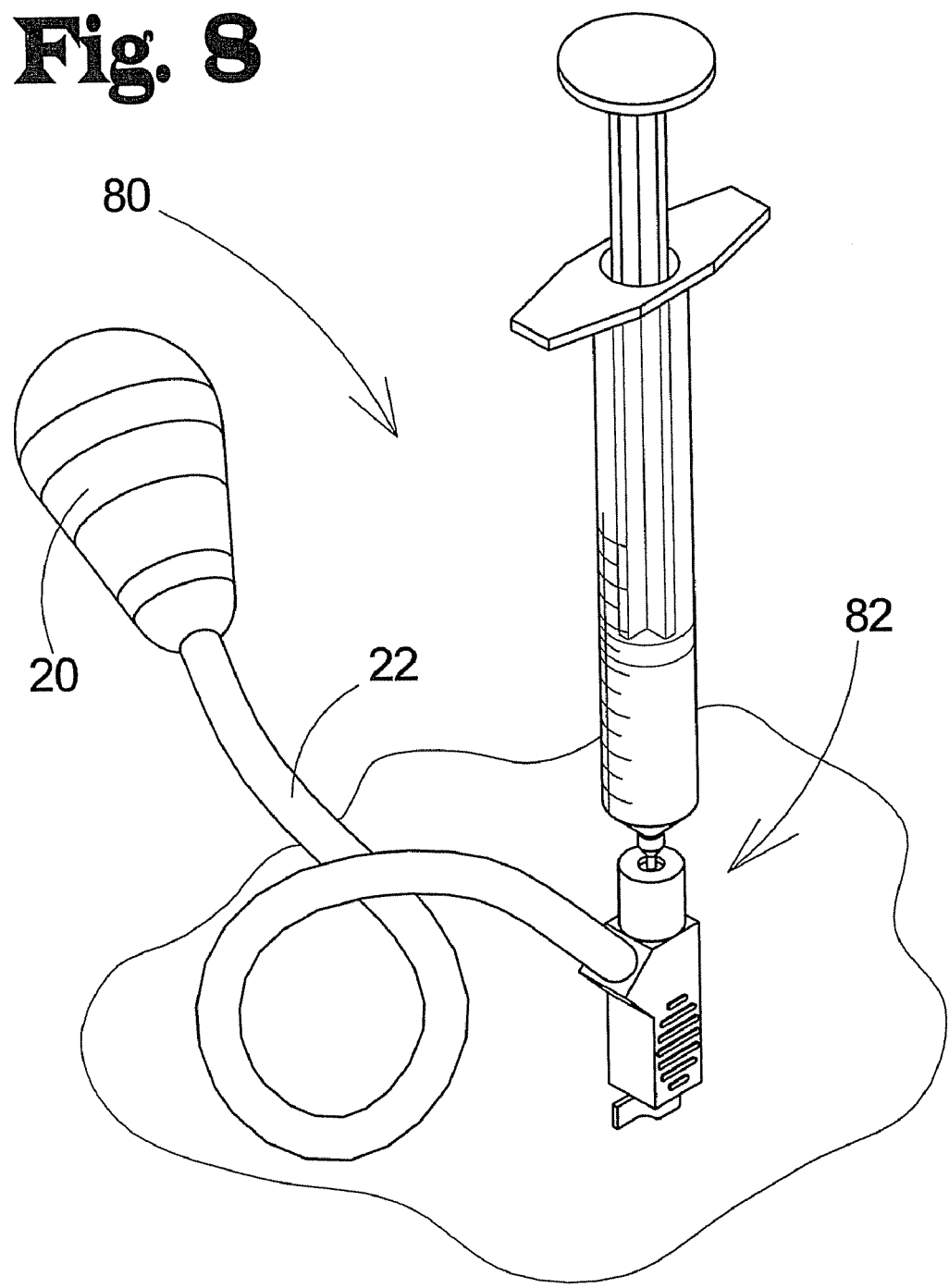
FIG. 8 is a schematic perspective view of an evacuating port aspiration system in accordance with principles of the present disclosure, including an evacuating port aspiration device mounted on the evacuating port device of FIG. 1.
Figure 9:
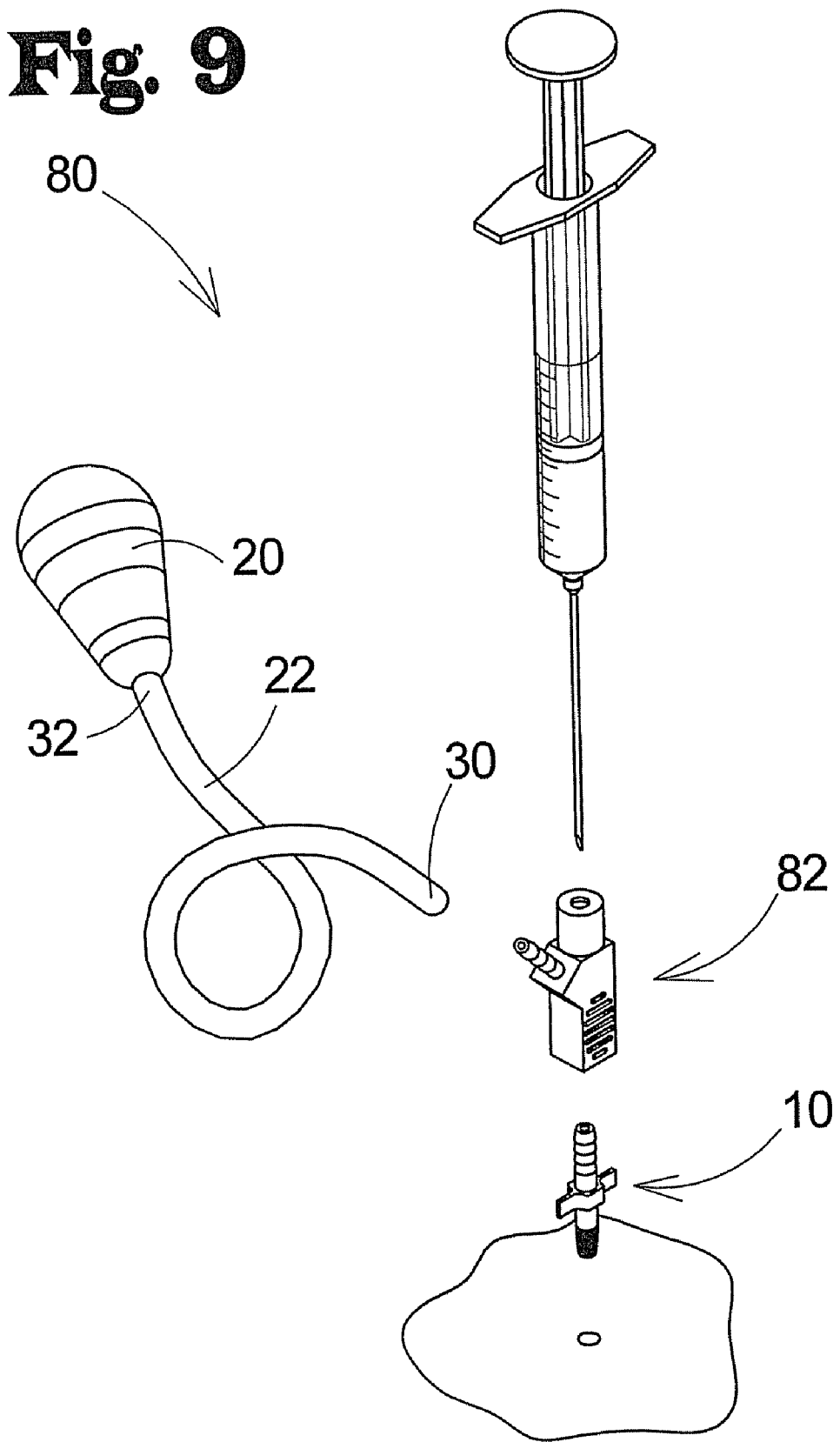
FIG. 9 is a schematic exploded perspective view of the system shown in FIG. 8.
Figure 10:
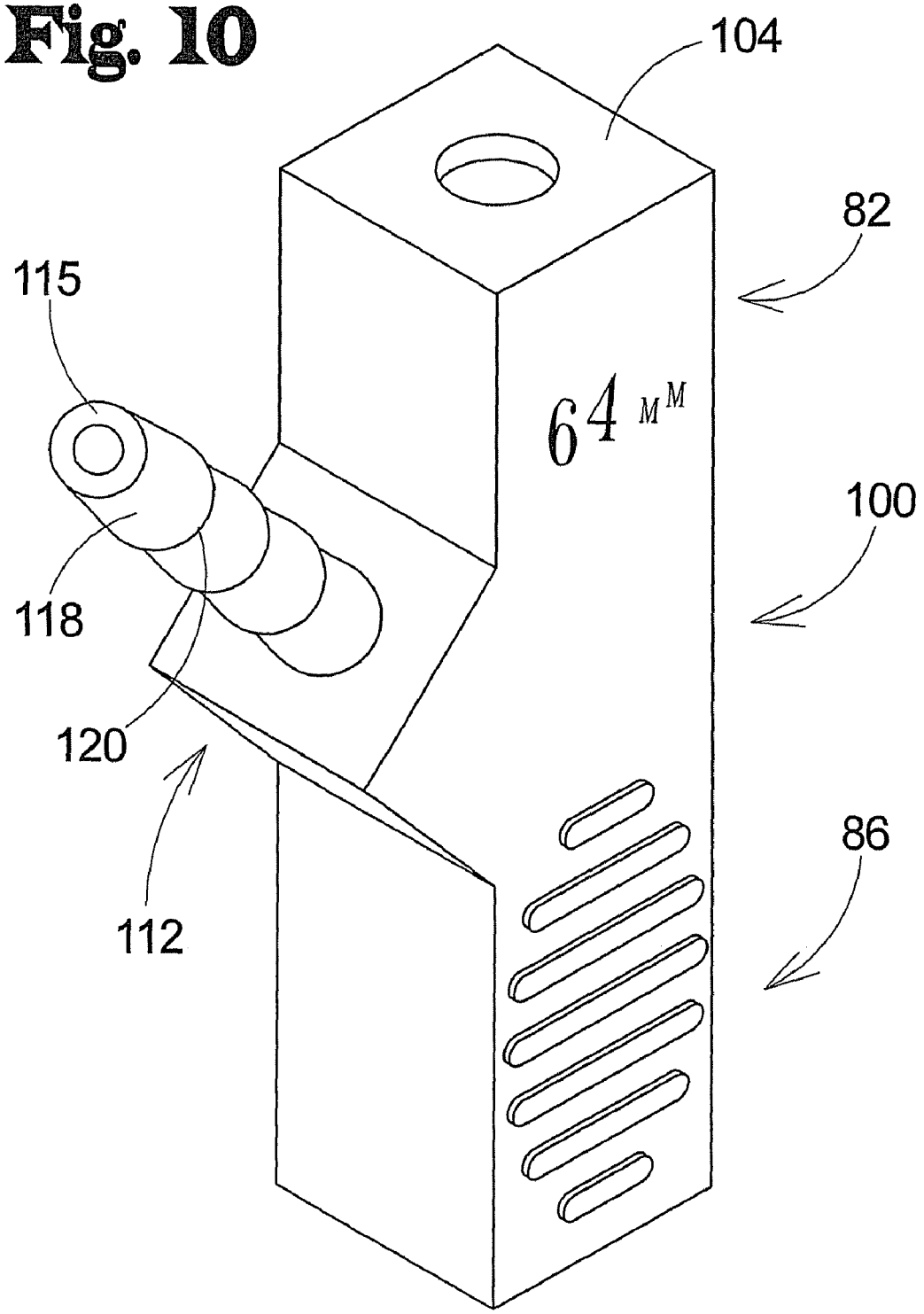
FIG. 10 is a schematic perspective view of the evacuating port aspiration device of FIG. 8.

The subdural evacuation portion aspiration system 80 includes an evacuation port aspiration device 82 that permits access to the evacuating lumen 42 and thus permits aspiration of the evacuation port device 10 when the port aspiration device 82 is mounted on the evacuation port device 10 (see FIGS. 8 through 10). The port aspiration device 82 defines an aspiration channel 84 (see FIGS. 11 and 12), and may be configured to create fluid communication between the aspiration channel 84 and the evacuation port lumen 42 when the port aspiration device 82 is mounted on the evacuation port device 10. The port aspiration device 82 may thereby become the conduit for receiving, for example, a needle or other instrument that is inserted into the port lumen 42 and optionally into the subcranial space of the patient, such as the subdural space.

In greater detail, the port aspiration device 82 may comprise a mounting portion 86 that is configured to mount on the evacuation port device 10. The mounting portion 86 may define a first portion 88 of the aspiration channel 84, and may include a socket 90 configured to receive a portion of the evacuation port device 10, such as, for example, the distal end 36 of the port device 10. The socket 90 may be in fluid communication with the first portion 88 of the aspiration channel 84. The mounting portion 86 terminates at a first end 92 of the port aspiration device 82. The mounting portion 86 may include a first perimeter wall 93 which may define the socket 90 so that the socket 90 comprises a portion of the aspiration channel 84. The socket 90 may have an enlarged width compared to a width of the first portion 88 of the aspiration channel 84.

The mounting portion 86 may also include a mounting structure 94 that is positioned on the socket 90 for removably mounting the distal end 38 of the tubular portion 40 of the evacuation port device 10 on the socket 90. The mounting structure 94 may be configured to removably grip the distal end of the evacuation port device 10, such as by engaging or gripping the retaining structure 50 of the evacuation port device 10 (although other manners of engagement may be employed). In one embodiment of the disclosure, the mounting structure 94 comprises a compressible material 96 positioned in the socket 90 for engaging the retaining structure 50 of the evacuation port device 10. The compressible material 96 may line a portion of an interior surface of the socket 90. The compressible material 96 may, for example, be configured in a hollow tubular shape, and may be substantially cylindrical. The compressible material 96 may be sized so that insertion of the distal end of the evacuation port device 10 at least partially compresses the compressible material 96 and creates a substantially air tight and fluid tight relationship between the lumen 42 of the port device 10 and the aspiration channel 84 of the port aspiration device 82. It will be recognized by those skilled in the art that other equivalent mounting structure designs may also be employed.

The port aspiration device 82 may also include an aspiration portion 100 for receiving an aspiration device, such as, for example, a needle or other instrument. The aspiration portion 100 may define a second portion 102 of the aspiration channel 84. The second portion 102 of the aspiration channel 84 may be axially aligned with the first portion 88 of the aspiration channel 84 such that the first and second portions 88, 102 of the aspiration channel 84 are configured to receive a needle (or other elongate instrument) therethrough. The aspiration portion 100 may terminate in a second end 104 of the aspiration device 82. The aspiration portion 100 may comprise a second perimeter wall 106 that is connected to the first perimeter wall 93.

Figure 11:
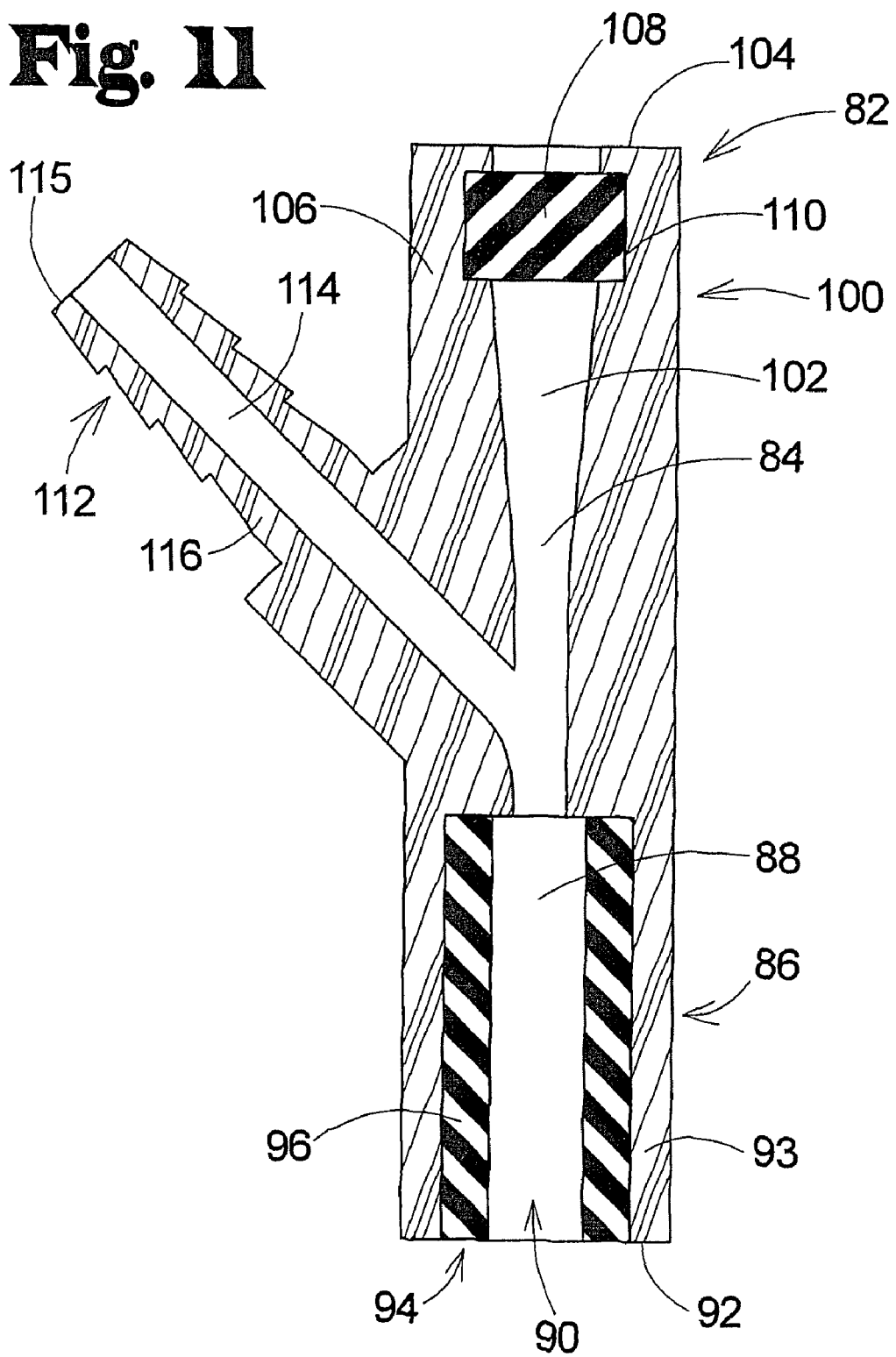
FIG. 11 is a schematic sectional view of the evacuating port aspiration device of FIG. 8.

A closing structure 108 may be provided on the aspiration portion 100 of the device 82 for closing the second portion 102 of the aspiration channel 84 (see FIG. 11). The closing structure 108 may close the aspiration channel 84 in an air tight and fluid tight manner. The closing structure 108 may extend across the aspiration channel 84. The closing structure 108 may be mounted on the second perimeter wall 106 of the aspiration portion, and may be seated in and extend into an annular groove 110 formed in the second perimeter wall 106. The closing structure 108 may be puncturable or be otherwise penetrated by a needle or other instrument. The closing structure 108 may be configured to reseal (or substantially reseal) itself after a puncturing needle is withdrawn from puncture of the closing structure. In some embodiments, the closing structure 108 may comprise a septum such as is employed on bottles holding liquid medicines, which are drawn from the bottle using a hypodermic needle. This closure or septum may comprise an elastomeric material, such as, for example, synthetic or natural rubber.

The port aspiration device 82 may further comprise a negative pressure connection portion 112 for connecting to a negative pressure source, such as through a conduit of the type described previously in this specification. The negative pressure connection portion 112 may define a third portion 114 of the aspiration channel 84. The third portion 114 of the aspiration channel 84 may extend along an axis that is skewed with respect to an axis of the first portion 88 of the aspiration channel. The negative pressure connection portion 112 may terminate in a third end 115 of the aspiration device 82. It should be recognized that although the illustrative embodiment includes a single negative pressure connection portion 112, two or more connection portions may be included on the port aspiration device 82, and the one or more connection portions are not necessarily limited to the purpose of providing a negative pressure connection.

In greater detail, the negative pressure connection portion 112 may comprise a third perimeter wall 116 that has an exterior surface 118. The third perimeter wall 116 may be connected to the first 93 and second 106 perimeter walls. The negative pressure connection portion 112 may further comprise a retaining structure 120 for engaging a conduit mounted on the negative pressure connection portion 112. The retaining structure 120 may include at least one annular barb formed on the exterior surface 118 adjacent to the third end 115 of the aspiration device 82 to engage the interior surface of a conduit having a flexible wall, to thereby releasably retain the conduit on the third end 115 of the port aspiration device 82.

In some embodiments of the port aspiration device 82, the distance between the first end 92 and the second end 104 of the port aspiration device 82 is a defined distance, so that the healthcare provider is able to calculate the approximate depth of penetration of the needle or other instrument into the skull cavity when the needle or instrument of a known length is fully inserted into the port aspiration device 82. The port aspiration device 82 may be provided with different defined distances between the first 92 and second 104 ends so that the desired length of the port aspiration device may be selected.

Optionally, as illustrated in FIG. 10 of the drawings, an indicia may be marked on the port aspiration device 82 to indicate the distance between the first end 92 and the second end 104 of the device 82 so that the user of the device 82 is able to know the defined distance without, for example, having to measure the distance. As noted above, knowledge of the distance between the first 92 and second 104 ends can assist in determining the length of the needle to use with the port aspiration device 82 or the position of a limiting structure 122 that will now be described.

Figure 12:
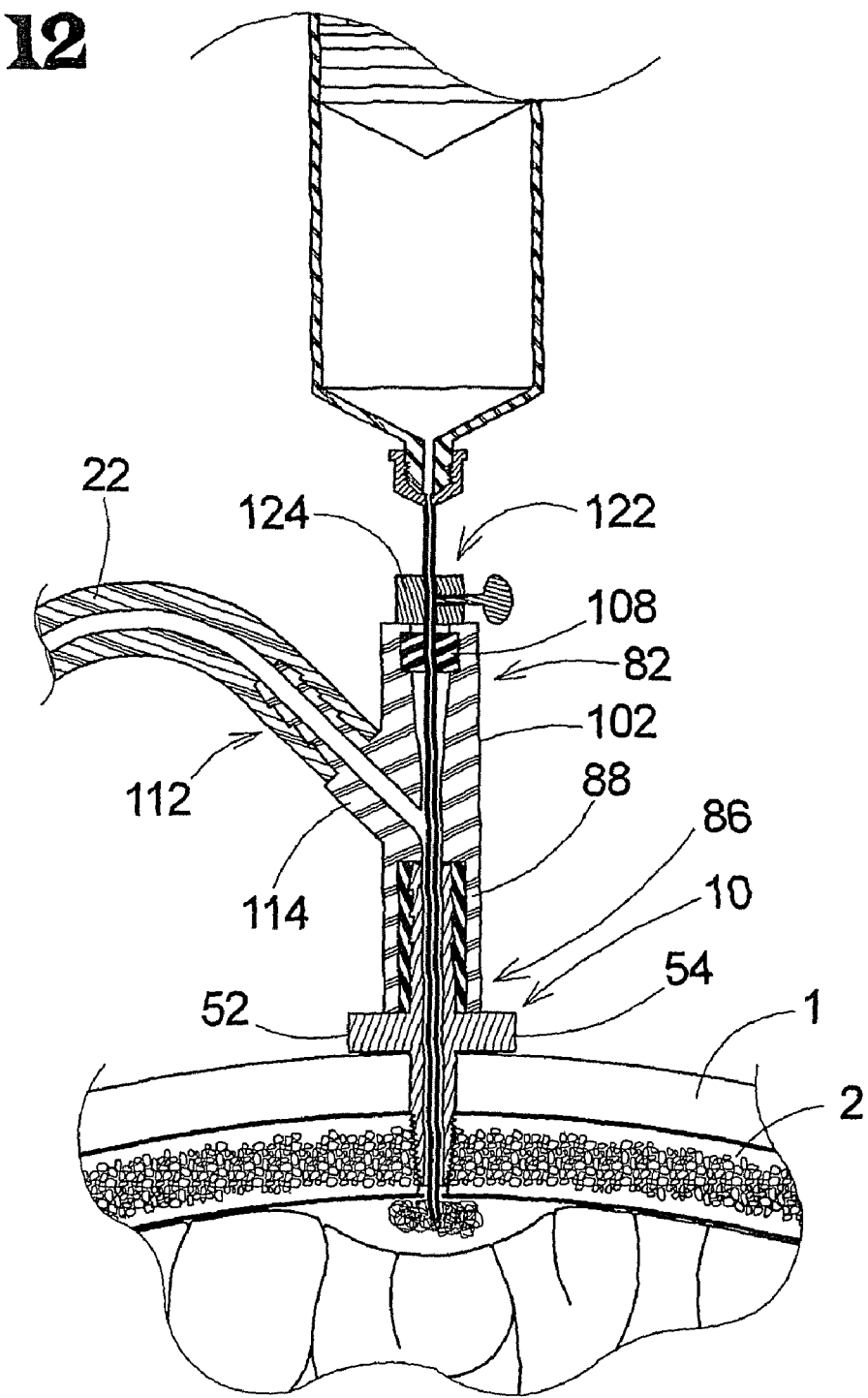
FIG. 12 is a schematic sectional view of the evacuating port aspiration system of FIG. 8 mounted on a patient's skull.
Figure 13:
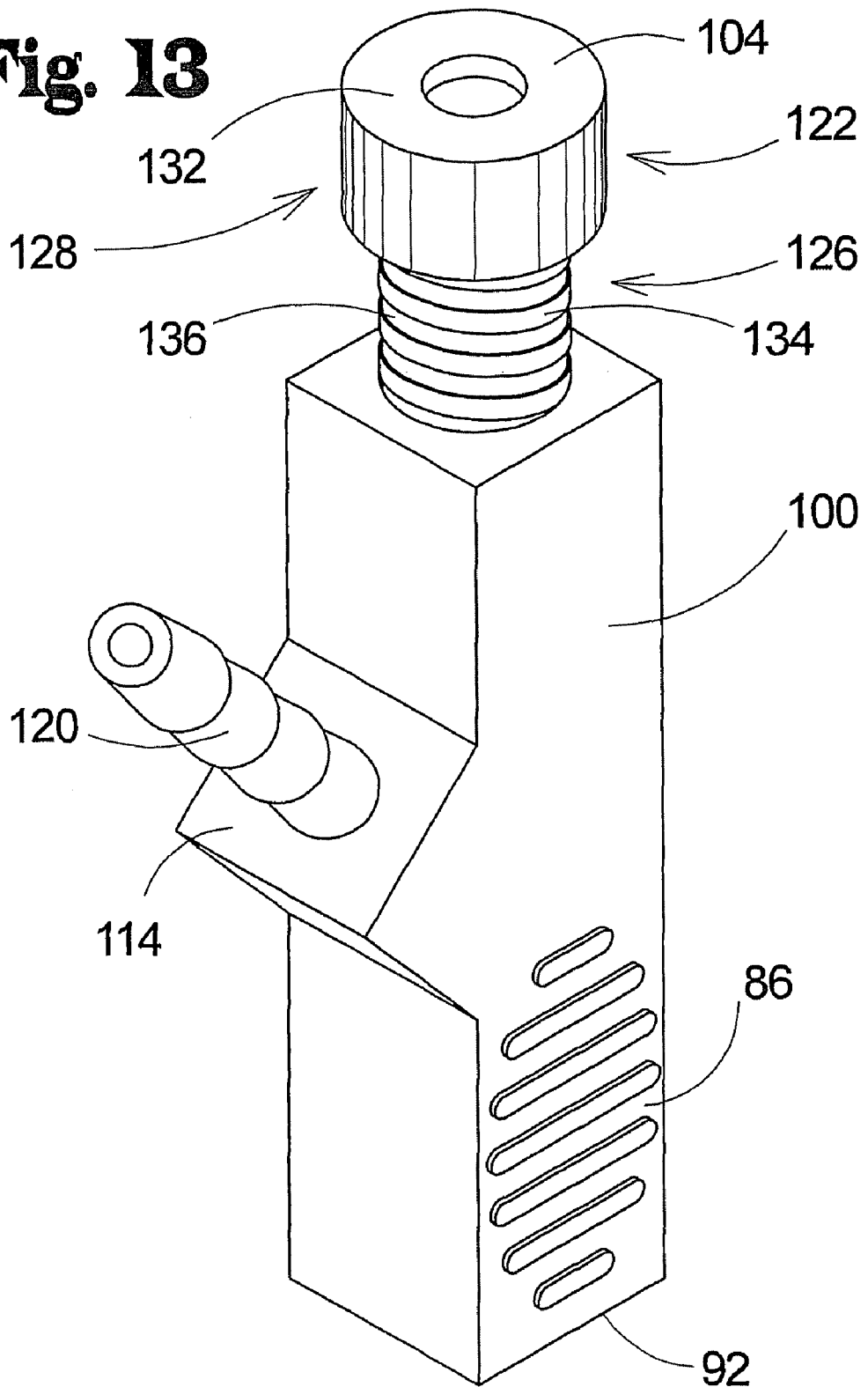
FIG. 13 is a schematic perspective view of another evacuating port aspiration device in accordance with principles of the present disclosure including a length adjustment structure.
Figure 14:
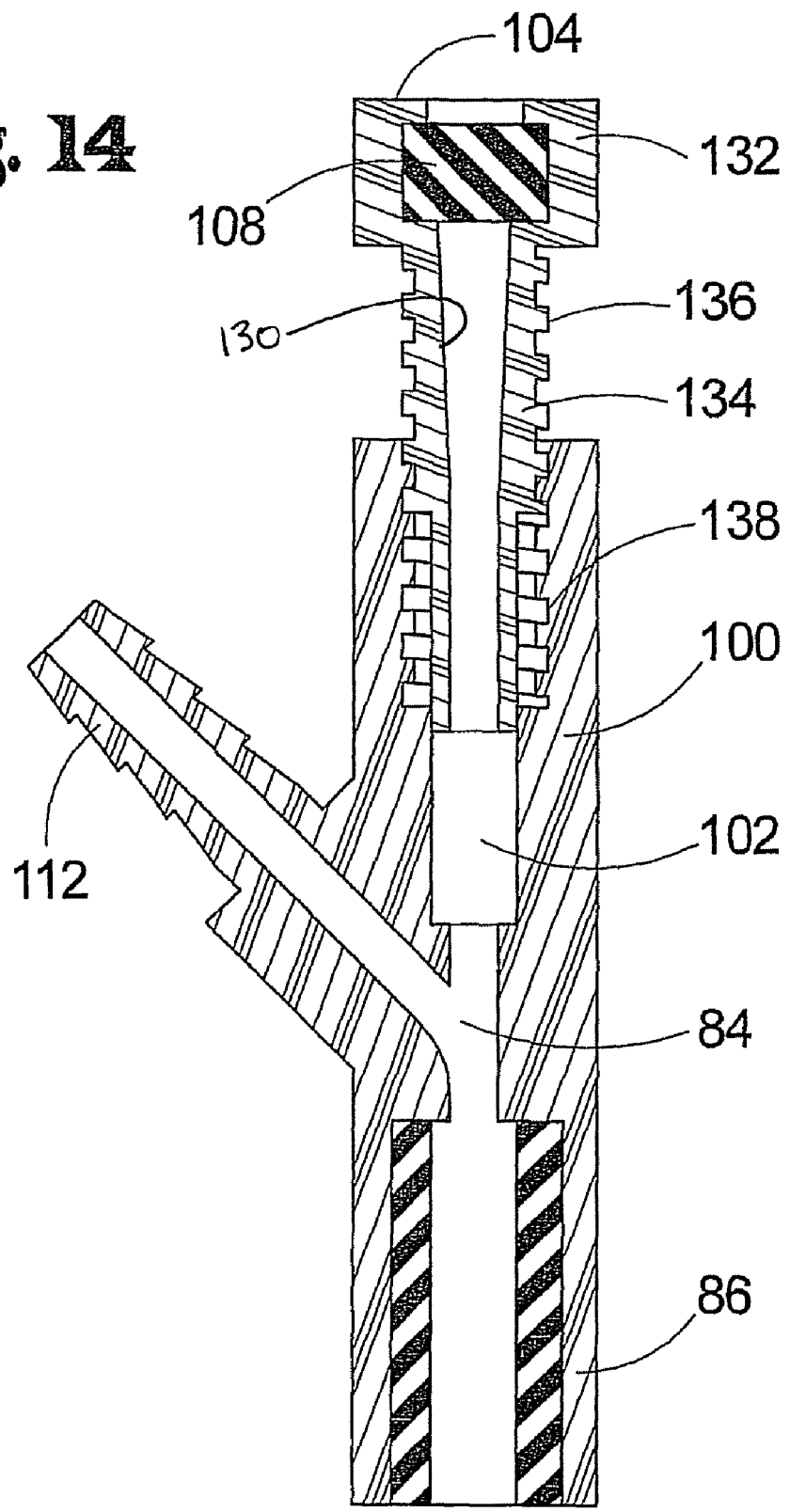
FIG. 14 is a schematic sectional view of the evacuating port aspiration device of FIG. 13.
Figure 15:
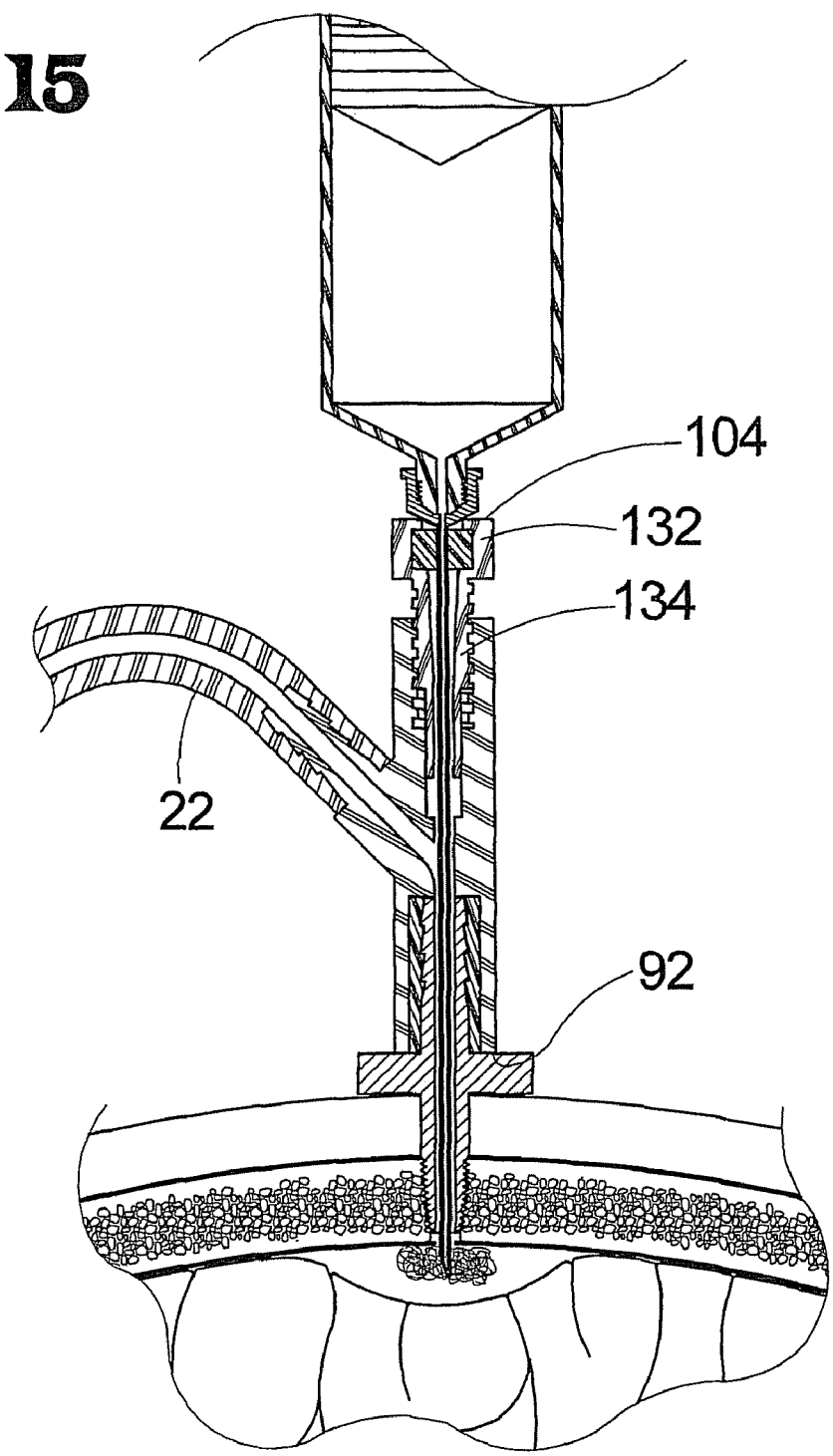
FIG. 15 is a schematic sectional view of another evacuating port aspiration system in accordance with principles of the present disclosure including the evacuating port aspiration device of FIG. 13.

In other embodiments of the port aspiration device 82, a limiting structure 122 may be provided on the device 82 that is capable of adjustably limiting a depth of insertion of a needle (or other instrument) into the evacuation port device 10 through the aspiration device 82 (see FIG. 12). Illustratively, the limiting structure 122 may comprise a stop collar 124 that is mountable on a needle (or other instrument) at an adjustable distance from a tip of the needle such that insertion of the needle brings the collar 124 into contact with the second end 104 of the port aspiration device 82 to limit further insertion of the needle into the aspiration channel 84.

In still other embodiments, the limiting structure 122 may comprise an adjustment structure 126 for adjusting an effective length of the mounting 86 and aspiration 100 portions of the port aspiration device 82. Illustratively, the adjustment structure 126 comprises an adjustable collar element 128 mounted on the aspiration portion 100 of the aspiration device 82 (see FIGS. 13 through 16). The adjustable collar element 128 may define a lumen 130 in fluid communication with the aspiration channel 84. The adjustable collar element 128 may comprise a collar 132, with the lumen 130 extending through the collar 132, and a column 134 mounted on the collar 132. The lumen 130 extends through the column 134. The column 134 may be at least partially inserted into the aspiration portion 100. The column 134 and the aspiration portion 100 may be coupled together in a manner that permits the degree of extension of the collar 132 from the aspiration portion 100 to be adjusted. In at least one embodiment, the column 134 has an exterior surface 136 that is threaded. The threaded exterior surface 136 of the column 134 may be engaged with a threaded interior surface 138 of the second portion 102 of the aspiration channel 84 such that rotation of the column 134 in a first rotational direction moves the collar 132 away from the aspiration portion 100 and rotation of the column 134 in a second rotational direction moves the collar toward the aspiration portion 100. Thus, rotation of the collar 132 and column 134 causes a change in the effective length of the aspiration device between the first and second ends. The closing structure 108 may be mounted on the column 134 to thus close the lumen 130 of the adjustable collar element 128, and thus the closing structure would not be present on the second portion 102 of the aspiration channel 84. Although a threaded coupling has been described, other manners of coupling the collar 132 and the column 134 to the aspiration portion 100 may be employed without departing from the disclosure.

Figure 16:
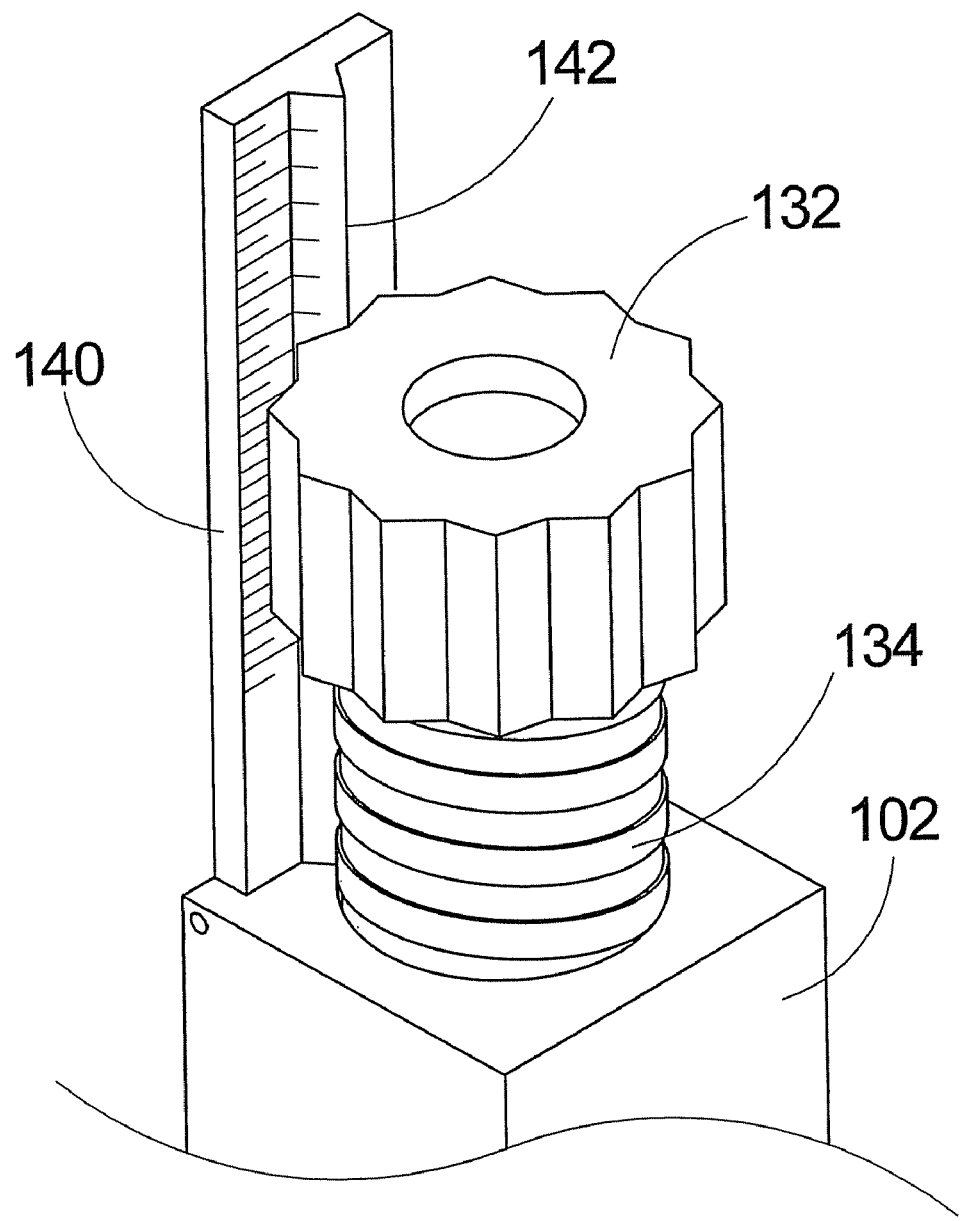
FIG. 16 is a schematic perspective view of another evacuating port aspiration device in accordance with principles of the present disclosure.

Optionally, a length indication device 140 may be provided for indicating the effective length of the port aspiration device 82 (see FIG. 16). The length indication device 140 may include graduations marked thereon that may be calibrated to indicate the distance between the first 92 and second 104 ends, or the total effective length of aspiration channel 84 of the aspiration device 82 and the lumen 42 of the evacuation port 10. The length indication device 140 may include structure 142 for interlocking with the collar 132 to lock the collar and column 134 against rotation once the desired adjustment has been achieved. In other embodiments of the disclosure, graduations or length indicating indicia may be marked on the portion aspiration device (such as on the exterior surface 136 of the column 134) so that the distance between the ends 92, 104 is discernable from the graduations as the degree of extension is adjusted.

Figure 17:
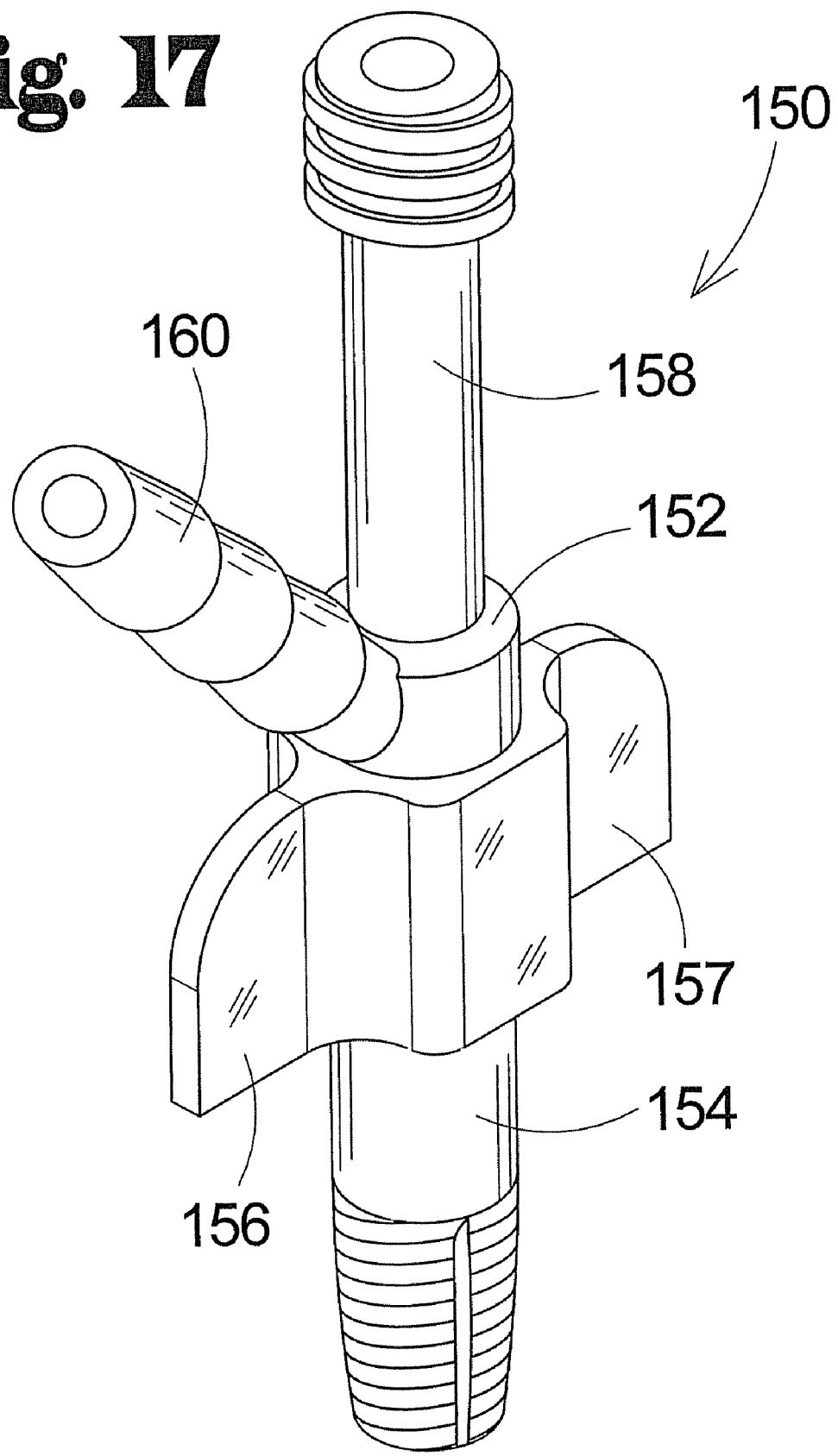
FIG. 17 is a schematic perspective view of a portion of another evacuating port aspiration system in accordance with principles of the present disclosure.

It should be realized that even though the evacuation port device 10 and the port aspiration device 82 as separate or separable parts is highly useful, the structural aspects of the port device 10 and the aspiration device 82 may also be implemented as a unified part that does not permit separation of the elements from each other. Thus, in patient applications for the evacuation port device where it is known that access to the subdural space will be needed while the port device is in place to, for example, apply medicine to the area or clear a blood clot, a combination structure of the devices such as is shown in FIGS. 17 and 18 of the drawings may be employed. Such an embodiment, designated by the reference number 150, may include any of the features described above, but may omit the structures employed to removably mount the port aspiration device to the evacuating port device. Further, the embodiment 150 may includes a unified body member 152 that may include structures that generally correspond to a tubular portion 154 and wings 156, 157 of the evacuating port aspect, and an aspiration portion 158 and a negative pressure portion 160 of the port aspiration aspect. The unified embodiment 150 may also include a cap member 162 that is removably mounted on the aspiration portion 158. A closing structure 164 may be mounted on the cap member 162 so that the closing structure 164 is thus removable from the unified body member 152. The cap member 162 may be removably mounted on the body member 152 by means of threads, such as exterior threads formed on the body member 152 and interior threads formed on the cap member 162. In some embodiments, the exterior threads on the body member 152 may be compatible with existing or standardized intravenous (IV) equipment to permit connection of IV equipment to the body member 152. The threaded mounting of the cap member 162 provides the benefit of adjustability of the overall length of the unified body member 152 between a first end 166 of the unified body member 152 and a second end 168 of the cap member 162, the significance of which has been discussed previously in this description. Other structures may be employed to secure the cap member 162 on the body member 152, or the cap member 162 may be omitted and the closing structure 164 may be positioned directly on the body member 152.

Another aspect of the disclosure is directed to a method of aspirating a subdural space within the skull of a patient, or other space in the body in which the evacuating port device 10 is mounted. The method may be useful when a blood clot or other accumulation of matter has become lodged in, or is otherwise obstructing, the evacuating lumen 42 of the port device 10. Such obstructions may also occur in the subdural space just outside the evacuating lumen 42, such as when an agglomeration too large to pass through the evacuating lumen is drawn by the negative pressure toward the port device 10. The obstruction may then be removed by aspiration or by dissolution. Optionally, medicines or other fluids may be applied to the subdural space by means of a needle using the port aspiration and the evacuating port devices, or an integral combination thereof.

The steps involved in positioning and placing the evacuating port device 10 have been outlined previously, and the description of the method of aspiration will commence from the point where the evacuating port device 10 has been installed on the patient. If a conduit 22 has been connected to the port device 10 such as at the distal end 36 of the tubular portion 40, an end of the conduit 22 is disconnected from the end of the tubular portion 40 to thereby free the distal end 30 of the port device 10. The port aspiration device 82 is then mounted on the evacuating port device 10, which may include creating a fluid communication between an aspiration channel 84 of the port aspiration device 82 and the evacuating lumen 42 of the evacuating port device 10. To accomplish this, the end 36 of the tubular portion 40 of the evacuating port device 10 may be inserted into the socket 90 formed by the mounting portion 86 of the port aspiration device 82. The end of the conduit 22 may be reconnected to the negative pressure connection portion 112 of the port aspiration device 82.

In some embodiments of the port aspiration device 82, an effective length of the aspiration device 82 between the first end 92 and the second end 104 may be adjusted. The adjustment may be effected in a manner suitable for the particular structure, such as in the illustrative embodiment, by rotating the adjustable collar element 128 mounted on the aspiration portion 100 to selectively extend or retract the adjustable collar 132 with respect to the aspiration portion of the port aspiration device 82. The effective length or distance between the first 92 and second 104 ends may be adjusted to affect the distance or degree to which the instrument or needle may be inserted into or through the port aspiration device 82 and the evacuating device 10, and therefore into the subdural space. The degree of penetration is dependent upon the effective length of the aspiration device 82 and the length of the needle. Optionally, the degree of penetration by the needle of known length, or the effective length of the aspiration device 82, may be adjusted according to a marking viewed on the length indication device 140.

In other embodiments of the disclosure, the method may include limiting the depth of penetration of the needle into the port aspiration device 82 by adjusting the position of the stop collar 124 on the needle itself.

An instrument, such as a hypodermic needle, may be positioned in the aspiration channel 84 of the port aspiration device 82. The needle may be inserted into the aspiration channel 84 through the aspiration portion 100 of the aspiration device. The needle may be inserted through the closing structure 108 in the aspiration channel 84 of the port aspiration device 82. The needle may continue through the evacuation lumen 42 of the evacuating port device 10. Once the end of the needle has reached the evacuating lumen 42, it may be used to remove an obstruction in the lumen 42 or in the subdural space, as well as to deliver medicine or other fluids to the subdural space.

Finally, it should be appreciated from the foregoing description that, except when mutually exclusive, the features of the various embodiments described herein may be combined with features of other embodiments as desired while remaining within the intended scope of the disclosure.

With respect to the above description then, it is to be realized that the optimum dimensional relationships for the parts of the disclosure, to include variations in size, materials, shape, form, function and manner of operation, assembly and use, are deemed readily apparent to one skilled in the art, and all equivalent relationships to those illustrated in the drawings and described in the specification are intended to be encompassed by the present disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure.

What is claimed is:

1. A method of aspirating a space within the body of a patient, comprising:
    mounting a subdural evacuating port device into the body of the patient, the subdural evacuating port device having an evacuating lumen in fluid communication with the space in the body; then
    mounting a port aspiration device on the subdural evacuating port device, including creating fluid communication between an aspiration channel of the port aspiration device and the evacuating lumen of the subdural evacuating port device, the port aspiration device comprising a mounting portion defining a first portion of the aspiration channel, and an aspiration portion defining a second portion of the aspiration channel, wherein the subdural evacuating port device extends into and releasably engages within a socket of the mounting portion;
    inserting an instrument through a closing structure in the aspiration channel of the port aspiration device so that the instrument is capable of entering the evacuating lumen of the subdural evacuating port device; and
    aspirating the space with the instrument.

2. The method of claim 1, wherein inserting the instrument includes inserting a needle into the aspiration channel of the port aspiration device and into the evacuating lumen of the subdural evacuating port device.

3. The method of claim 2, wherein insertion of the needle is limited in depth of penetration by adjusting a position of a stop collar on the needle.

4. The method of claim 1, additionally including adjusting an effective length of the port aspiration device between first and second ends of the port aspiration device.

5. The method of claim 1, additionally including disconnecting an end of a conduit from the subdural evacuating port device and connecting the end of the conduit to a negative pressure connection portion of the port aspiration device.

6. The method of claim 1, additionally including:
    mounting a rigid tubular portion of the subdural evacuating port device into a hole in a skull of a patient.

7. The method of claim 6, wherein mounting the rigid tubular portion includes forming threads in a skull of the patient with rotation of the rigid tubular portion.

8. The method of claim 7, wherein mounting the rigid tubular portion includes rotating the evacuation port device using winged extensions projecting outwardly from a medial point between a distal end and a proximal end of the subdural evacuating port device.

9. The method of claim 1, wherein the aspiration channel includes a first portion, a second portion, and a third portion, the second and third portions diverging from one another in extension from the first portion, and further wherein upon mounting of the port aspiration device on the subdural evacuating port device, the first portion, the second portion, and the evacuating lumen combine to rigidly define a common, linear central axis.

10. The method of claim 1, wherein mounting the port aspiration device on the subdural evacuating port device includes at least partially compressing a compressible material positioned in the socket with a distal portion of the evacuating port device.

11. The method of claim 1, wherein mounting the port aspiration device on the subdural evacuating port device includes engaging a retaining structure of the subdural evacuating port device within the socket.

12. A method of aspirating a space within the body of a patient, comprising:
    providing a subdural evacuating port device having an evacuating lumen in fluid communication with the space in the body;
    mounting a port aspiration device on the subdural evacuating port device, including creating fluid communication between an aspiration channel of the port aspiration device and the evacuating lumen of the subdural evacuating port device;
    inserting an instrument through a closing structure in the aspiration channel of the port aspiration device so that the instrument is capable of entering the evacuating lumen of the subdural evacuating port device; and
    aspirating the space with the instrument; and
    adjusting an effective length of the port aspiration device between first and second ends of the port aspiration device,
    wherein adjusting the effective length includes rotating an adjustable collar element mounted on an aspiration portion to selectively extend or retract the adjustable collar with respect to the aspiration portion of the port aspiration device.

13. The method of claim 12, wherein adjusting the effective length includes aligning the adjustable collar with a selected marking on a length indication device including indicia indicating the effective length of the port aspiration device at various degrees of extension of the collar.

* * * * *